(12) United States Patent
Wiltshire et al.

(10) Patent No.: US 9,211,209 B2
(45) Date of Patent: Dec. 15, 2015

(54) OSTOMY APPLIANCE

(75) Inventors: Neil Wiltshire, Birmingham (GB); Eric Davison, Birmingham (GB)

(73) Assignee: Salts Healthcare, Ltd. (GB)

( * ) Notice: Subject to any disclaimer, the term of this patent is extended or adjusted under 35 U.S.C. 154(b) by 551 days.

(21) Appl. No.: 12/934,049

(22) PCT Filed: Mar. 11, 2009

(86) PCT No.: PCT/GB2009/000657
§ 371 (c)(1),
(2), (4) Date: Jan. 4, 2011

(87) PCT Pub. No.: WO2009/118510
PCT Pub. Date: Oct. 1, 2009

(65) Prior Publication Data
US 2011/0160684 A1    Jun. 30, 2011

(30) Foreign Application Priority Data

Mar. 26, 2008 (GB) .................................. 0805483.5

(51) Int. Cl.
*A61F 5/44* (2006.01)
*A61F 5/448* (2006.01)

(52) U.S. Cl.
CPC ...................................... *A61F 5/448* (2013.01)

(58) Field of Classification Search
CPC ... A61L 24/08; A61L 24/043; A61L 2400/14; A61L 15/46; A61L 2300/404; A61L 24/00; A61F 5/445; A61F 5/44; A61F 5/4404–5/4408; A61F 5/441–5/443; A61F 5/448; A61F 5/449; A61F 5/451–5/455; A61F 2005/4455–2005/4495; A61F 13/0203; A61F 13/0226; A61F 13/0269; A61F 2013/00978; A61M 25/02; A61M 2025/0213
USPC ......... 604/317, 322–345, 348, 352, 304–308, 604/17
See application file for complete search history.

(56) References Cited

U.S. PATENT DOCUMENTS

| 4,952,618 | A | * | 8/1990 | Olsen | 524/17 |
| 5,520,670 | A | * | 5/1996 | Blum | 604/338 |
| 6,537,261 | B1 | * | 3/2003 | Steer et al. | 604/342 |
| 2007/0005032 | A1 | * | 1/2007 | Shan et al. | 604/342 |

OTHER PUBLICATIONS

International Search Report mailed May 18, 2009, for International Application No. PCT/GB2009/000657.

* cited by examiner

*Primary Examiner* — Jason Flick
*Assistant Examiner* — Ned T Heffner
(74) *Attorney, Agent, or Firm* — Colin P. Cahoon; Shaukat A. Karjeker; Carstens & Cahoon, LLP

(57) ABSTRACT

A two piece ostomy appliance having a first part (bodyside part) adapted for securing to the body of a user, and second part (pouch part) that is releaseably secured to the first part. The pouch part has a pouch flange which has an opening communicating with an interior of the pouch; and a bodyside flange with an opening and a hydrocolloid layer for securing the bodyside flange to the stoma of a user. The bodyside flange has a location projection receivable in a recess in a part of the pouch flange to align the opening of the pouch flange with the opening of the bodyside flange. A surface of the pouch flange has an adhesive to adhere the pouch flange to the bodyside flange. The recess of the pouch flange is located at the periphery of the pouch flange, extending away from the opening in the pouch flange.

9 Claims, 3 Drawing Sheets

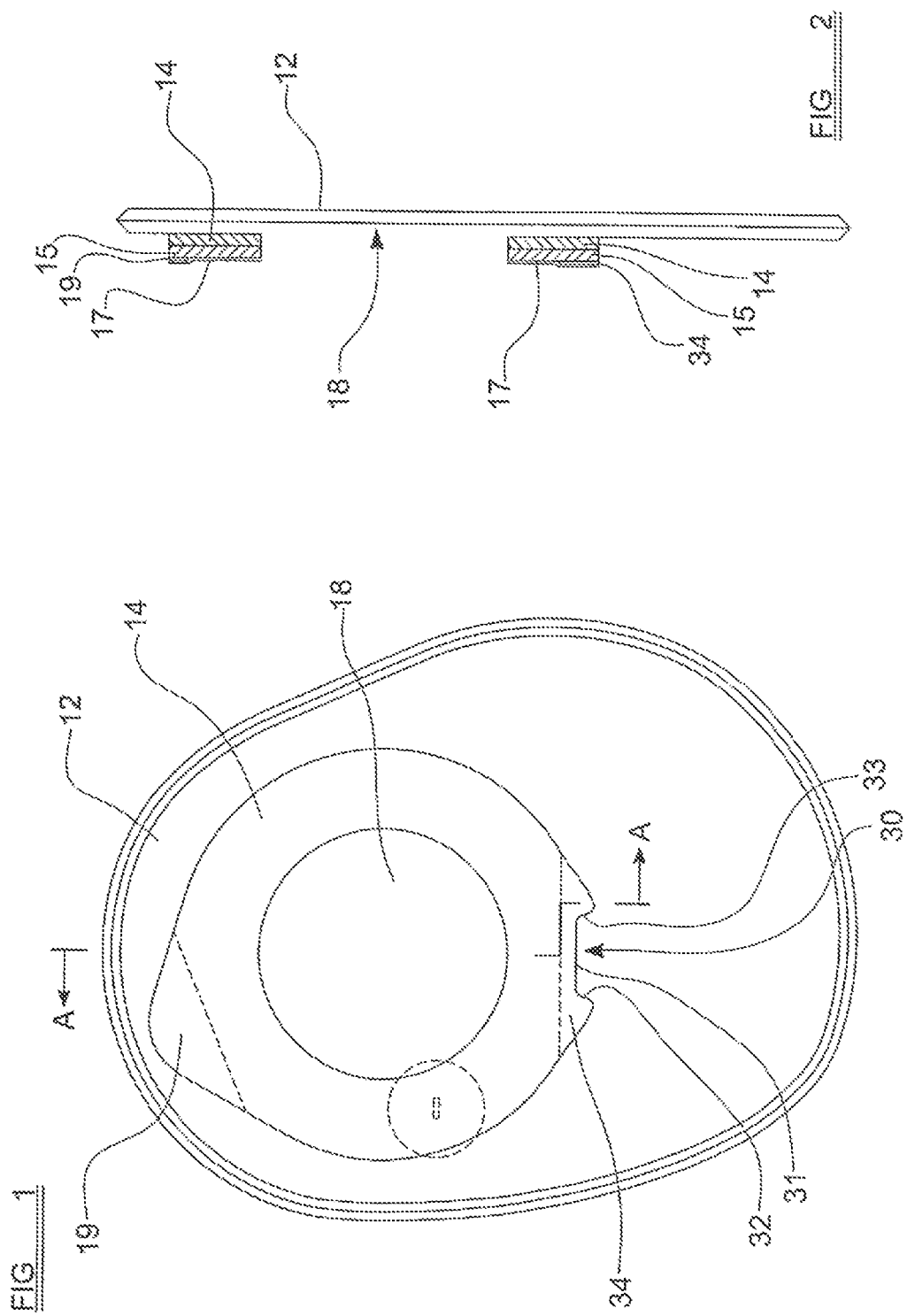

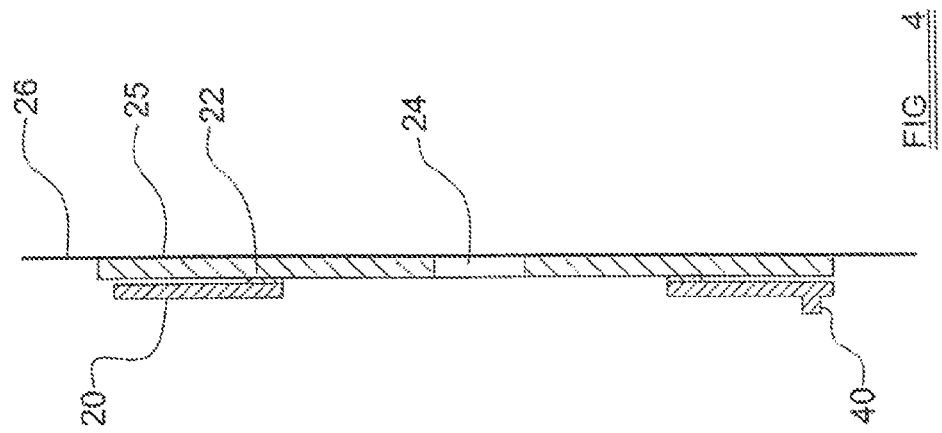
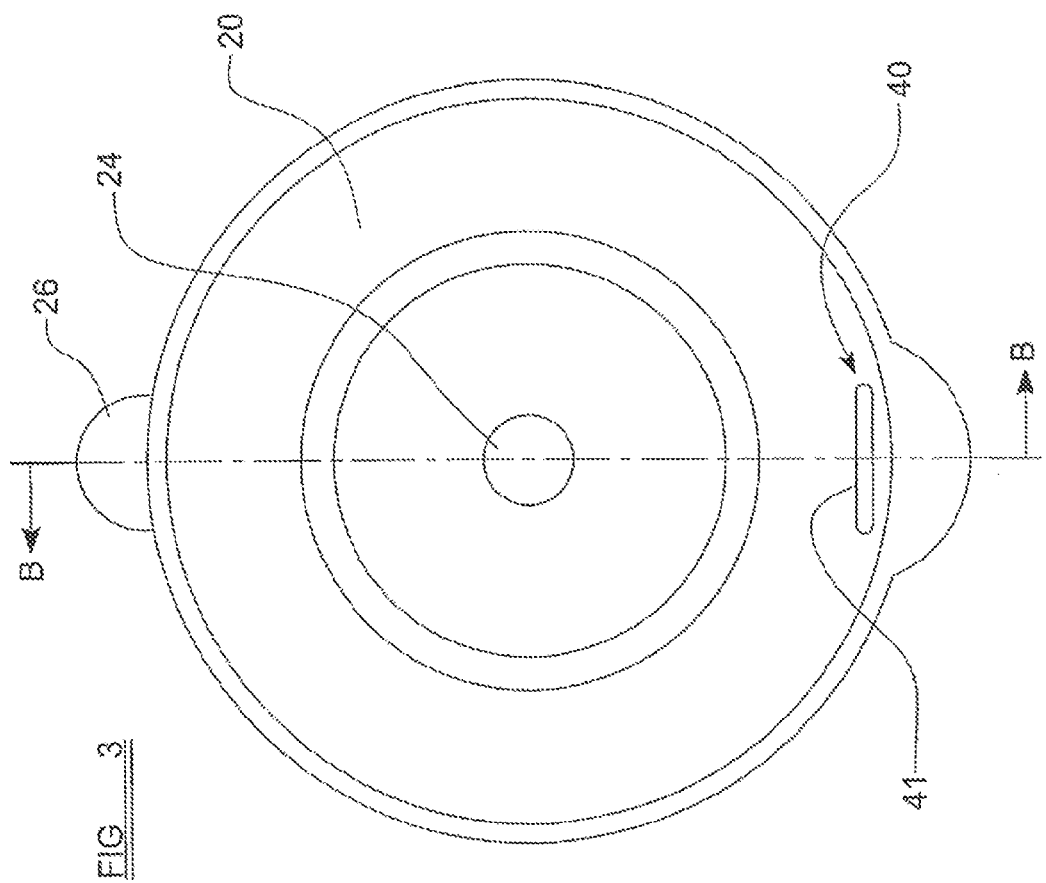

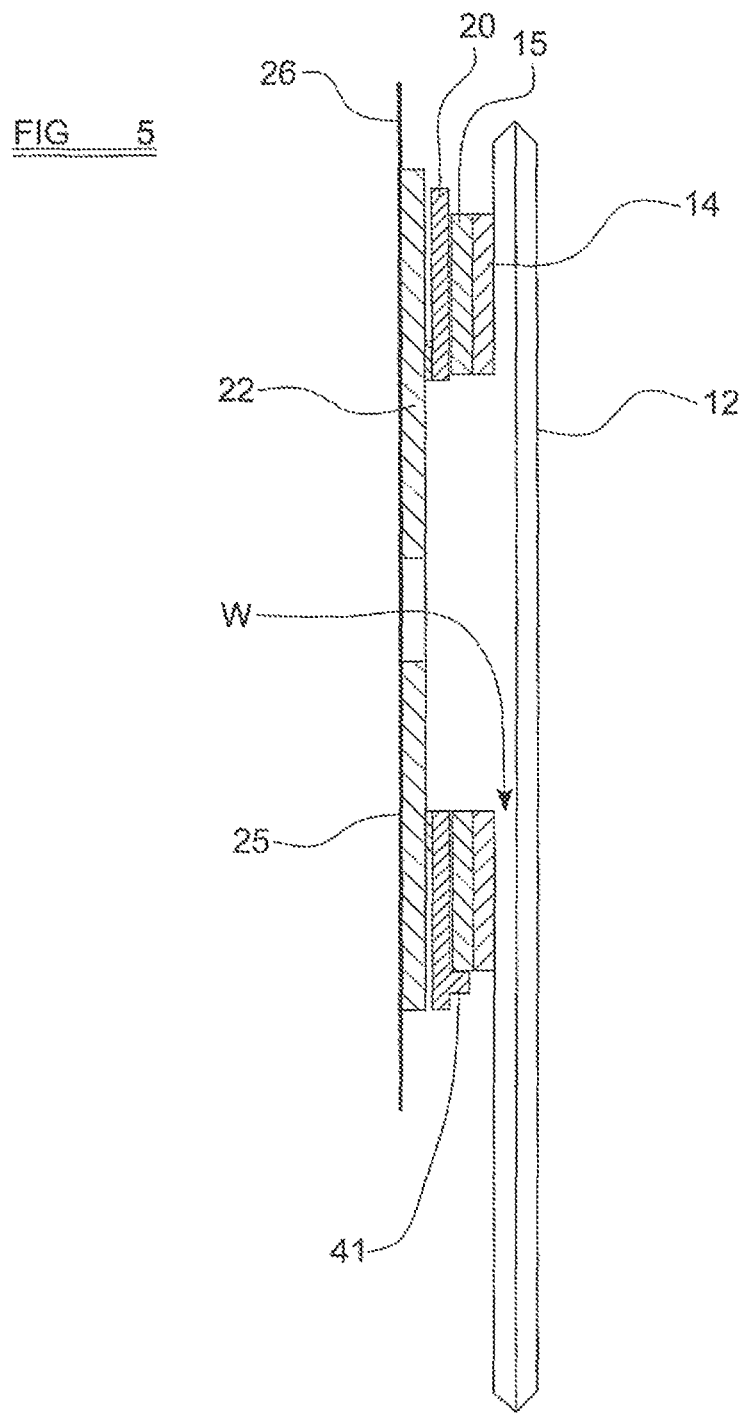

OSTOMY APPLIANCE

FIELD OF THE INVENTION

The invention relates to ostomy appliances, and in particular to ostomy appliances that have a first part (bodyside part) adapted for securing to the body of a user, and second part (pouch part) that is releaseably secured to the first part.

BRIEF SUMMARY OF THE INVENTION

Such ostomy appliances are known and are referred to as two piece appliances. The manner of securing the pouch to the bodyside part be adhesive or by means of some form of engagement system with co-operating formations on the bodyside part and on the pouch. Many prior art products suffer from the problem that users, who are often elderly and thus have relatively poor eyesight and/or are not very dextrous, have difficulty aligning the pouch with the bodyside part to ensure good connection, and thus an unobstructed fluid passage between the body side part and the pouch. This can lead to leaks and poor customer satisfaction.

It is an aim of the present invention to provide an alternative two piece ostomy appliance which seeks to mitigate the above described problem.

According to a first aspect of the present invention there is provided an ostomy appliance having:
  a pouch for receipt of waste;
  a pouch flange connected to the pouch, the pouch flange having an opening communicating with an interior of the pouch; and
  a bodyside flange with an opening and a hydrocolloid layer for securing the bodyside flange to a body of a user around their stoma, the bodyside flange including a location projection which is receivable in a recess in a part of the pouch flange to align the opening of the pouch flange relative to the opening of the bodyside flange;
  wherein a surface of the pouch flange which in use faces the bodyside flange includes an adhesive for adhering the pouch flange to the bodyside flange,
  characterised in that the recess is positioned at a periphery of the pouch flange and extends outwardly away from the opening communicating with an interior of the pouch.

The invention provides the advantage that the locating projection on the bodyside flange assists the user in locating the pouch flange accurately with respect to the bodyside flange by feel rather than sight, so that the opening in the bodyside flange is aligned relative to the opening in the pouch flange.

BRIEF DESCRIPTION OF THE DRAWINGS

Further features of the invention are set out in the claims appended hereto.

Examples of the invention will now be described by way of example only with reference to the accompanying drawings, of which:—

FIG. 1 is a front view of a pouch and pouch flange in accordance with the present invention;

FIG. 2 is a cross-sectional view of the pouch and pouch flange of FIG. 1 through the plane A-A;

FIG. 3 is a front view of bodyside flange in accordance with the present invention;

FIG. 4 is a cross-sectional view of the bodyside flange of FIG. 3 through the plane B-B; and FIG. 5 is a side view of the pouch flange and bodyside flange connected to each other.

DETAILED DESCRIPTION OF EXEMPLARY EMBODIMENTS OF THE INVENTION

Referring to figures, these show an ostomy appliance which has two main parts: a) pouch-side part including a pouch 12 for receipt of waste and a pouch flange 14 connected thereto; and b) a bodyside part including a bodyside flange 20.

The pouch flange 14 is substantially annular and is connected to the pouch 12 by a suitable adhesive, by heat welding or any other suitable joining method. The pouch flange 14 has an opening 18, substantially centrally therethrough which communicates with an interior 20 of the pouch 12. The components parts of the pouch 12 are well known in the art and will therefore not be discussed in any further detail herein. A surface of the pouch flange 14 which in use faces a user includes an adhesive layer 15 for adhering the pouch flange 14 to a bodyside flange 20 (discussed below). The adhesive layer 15 is strong enough to hold the pouch flange 14, and hence the pouch 12, relative to the bodyside flange 20, but permits the two flanges to be separated when it is required to remove the pouch 12 for emptying and/or to replace the pouch 12 with a fresh one. Whilst the pouch flange 14 is not in use, the adhesive layer 15 is covered by a removable cover 17, to maintain the integrity of the adhering properties of the layer 15.

The pouch flange 14 has a tab portion 19 at its uppermost end (in normal use), the surface of which is non-adhesive, either as a result of no adhesive being present at that portion of the flange 14 or as a result of a cover which is adhered to the tab portion 19. The non-adhesive characteristics of the tab portion 19 permit a user to grasp an adjacent portion of the cover 17, so that the cover 17 can be removed (discussed in detail later). The tab portion 19 also acts as a means for removing the pouch flange 14 from the bodyside flange 20.

The pouch flange 14 includes a recess 30 which in the present example is positioned at a periphery of the pouch flange 14. The recess 30 extends, substantially radially outwardly away from the opening 18. The recess 30 has a pair of side walls 32, 33 which are connected by a substantially flattened base wall 31. The side walls 32, 33 extend away from each other as they extend away from the opening 18.

A region of the surface of the pouch flange 14 which surrounds the recess 30 is non-adhesive. In the present example, this is achieved by adhering a cover 34 to the surface surrounding the recess 30. The outermost surface of the cover 34 is non-adhesive, thus ensuring that the cover 17 does not adhere to that region of the pouch flange 14.

As discussed above, the appliance also includes a bodyside flange 20 which is also annular. The bodyside flange 20 has a hydrocolloid layer 22 for securing the bodyside flange 20 to a body of a user around their stoma, and a opening 24 therethrough to provide for fluid communication between the user's stoma and the opening 18 in the pouch flange 14. The opening 24 can be increased in size by cutting the hydrocolloid layer 22, as is well known in the art. The hydrocolloid layer 22 is covered by a removable cover 25 which has a tab portion 26 for assisting in removal of the cover 25.

The bodyside flange 20 also includes a location projection 40 which is positioned at a periphery of the flange 20. The location projection 40 is an elongate substantially straight ledge, which extends substantially perpendicularly away from a general plane of the flange 20. A surface 41 of the location projection 40 which faces the opening 24 is flattened.

In use, the location projection 40 is received in the recess 30 so that the opening 18 of the pouch flange 14 is aligned relative to the opening 24 of the bodyside flange 20. This is achieved as follows.

The bodyside flange 20 is adhered to a user's skin such that the opening 24 is aligned with, and, if possible, receives the user's stoma. The hydrocolloid layer 22 (having had the cover 25 removed therefrom) adheres to the user's skin so as to provide a comfortable, strong and water-tight seal. Ideally, the bodyside flange 20 should be positioned on the user such that, when the user is standing upright, the flattened surface 41 of the location projection 40 is vertically beneath a centre of the opening and such that the flattened surface 41 is substantially horizontal.

The user then positions the pouch flange 14 by moving it downwardly until the flattened base wall 31 engages the flattened surface 41 of the location projection 40. Once the location projection 40 is received in the recess 30, the pouch flange 14 is aligned relative to the bodyside flange 20 such that opening 18 is also aligned relative to the opening 24. The user then removes the cover 17, by grasping the tab portion 19 and pulling the tab portion outwardly and downwardly, until the cover 17 is completely removed. The user then pivots the pouch flange 14 towards the bodyside flange 20, using the flattened surface 41 of the location projection 40 as a fulcrum, until the pouch flange 14 is adhered completely to the bodyside flange 20. Alternatively, the user may remove the cover 17 partially or completely before engaging the flattened surface 41 of the location projection 40 with the flattened base wall 31 of the recess 30.

The present invention is advantageous over known designs because, when the location projection 40 is fully received in the recess 30, rotational movement of the pouch flange 14 and bodyside flange 20 relative to each other, about an axis which extends substantially perpendicularly through the flanges 14, 20 (more particularly about an axis which extends substantially through the flanges in a vicinity of the recess 30), is inhibited. This helps the user ensure that the flanges 14, 24 are aligned before they are adhered to each other. In addition, the pair of opposing side walls 32, 33 inhibit lateral movement of the pouch flange 14 relative to the bodyside flange 20, thus providing further assurance for the user that the flanges 14, 20 are correctly aligned.

The provision of the non-adhesive region, in the present example the cover 34, surrounding the recess 30 allows for a user to make slight adjustments of the position of the pouch flange 14 relative to the bodyside flange 20 when engaging the location projection 40 in the recess 30, because the region surrounding the recess will not adhere to the bodyside flange 20. The cover 34 also ensures that the user can easily remove the cover 17 without having to disengage the projection 40 from the recess.

It should be appreciated that the adhesive layer 15 and its cover 17 could, alternatively, be provided on the bodyside flange 20, rather than on the pouch flange 14. In that case, it would be desirable for a region surrounding the location projection 40 (at least the region adjacent the flattened surface 41) to be non-adhesive, for the same reasons as mentioned above regarding the cover 34.

The materials from which the embodiments of the invention may be constructed are not limited in any way except by the properties of the materials themselves. However, examples of suitable materials are:
for the pouches themselves one or more layers of ethylene vinyl acetate (EVA) and a barrier layer such as polyvinylidene chloride (PVDC);
for foam elements, polyethylene foam;
for the injection moulded plastic flanges, ethylene vinyl acetate (EVA) or polyethylene.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An ostomy appliance having:
a pouch for receipt of waste;
a pouch flange connected to the pouch, the pouch flange having an annular portion with an opening communicating with an interior of the pouch and having a recess located in a lower portion of a perimeter of the pouch flange, the recess having a pair of opposed side walls and an upper wall, and
a bodyside flange including an opening and having a hydrocolloid layer for securing the bodyside flange to a body of a user around a stoma, the bodyside flange including an elongate substantially straight location projection receivable in the recess in the perimeter of the pouch flange to bring into alignment the opening of the pouch flange relative to the opening of the bodyside flange,
wherein the elongate substantially straight location projection forms a ledge which extends substantially perpendicularly away from a general plane of the bodyside flange and extends across the bodyside flange,
wherein a surface of the pouch flange which in use faces the bodyside flange includes an adhesive for adhering the pouch flange to the bodyside flange, and
wherein the recess of the pouch flange is open to receive therein the location projection of the bodyside flange, from below the recess, such that the opposed side walls of the recess guide the location projection to engage the upper wall of the recess, thereby engaging the pouch flange and orienting the pouch relative to the bodyside flange.

2. An ostomy appliance according to claim 1 wherein when the location projection is received in the recess, rotational movement of the pouch flange and bodyside flange relative to each other, about an axis which extends substantially perpendicularly through the flanges, is inhibited.

3. An ostomy appliance according to claim 1 wherein when the location projection is received in the recess, angular movement of the pouch flange and bodyside flange relative to each other, about an axis which extends substantially perpendicularly through the flanges in a vicinity of the recess, is inhibited.

4. An ostomy appliance according to claim 1 including a removable cover member which covers the adhesive surface of the pouch flange prior to use.

5. An ostomy appliance according to claim 1 wherein another region of the surface of the pouch flange which surrounds the recess is non-adhesive.

6. An ostomy appliance according to claim 1 wherein a region of the surface of the pouch flange, which in use faces the bodyside flange, surrounds the recess and is adhesive and covered by a cover, the outermost surface of which cover is non-adhesive, the cover intended to remain in situ when the flanges are adhered to each other.

7. An ostomy appliance according to claim 1 wherein the pair of opposing side walls of the recess inhibit lateral movement of the pouch flange relative to the bodyside flange.

8. An ostomy appliance according to claim 7 wherein the side walls of the recess extend away from each other as they extend away from the opening communicating with an interior of the pouch.

9. An ostomy appliance according to claim 8 wherein the side walls extend away from the opening communicating with an interior of the pouch in a general plan of the pouch flange.

* * * * *